(12) United States Patent
Wolfram

(10) Patent No.: US 8,129,337 B2
(45) Date of Patent: Mar. 6, 2012

(54) COMPOSITIONS COMPRISING EPIGALLOCATECHIN GALLATE AND PROTEIN HYDROLYSATE

(75) Inventor: Swen Wolfram, Waldshut-Tiengen (DE)

(73) Assignee: DSM IP Assets B.V., Heerlen (NL)

( * ) Notice: Subject to any disclaimer, the term of this patent is extended or adjusted under 35 U.S.C. 154(b) by 761 days.

(21) Appl. No.: 11/883,051

(22) PCT Filed: Feb. 2, 2006

(86) PCT No.: PCT/EP2006/050623
§ 371 (c)(1),
(2), (4) Date: Aug. 21, 2007

(87) PCT Pub. No.: WO2006/082222
PCT Pub. Date: Aug. 10, 2006

(65) Prior Publication Data
US 2008/0119389 A1    May 22, 2008

(30) Foreign Application Priority Data
Feb. 3, 2005  (EP) .................................... 05100755

(51) Int. Cl.
*A61K 38/16*        (2006.01)

(52) U.S. Cl. ............................. 514/5.7; 514/27; 514/456
(58) Field of Classification Search .................... None
See application file for complete search history.

(56) References Cited

U.S. PATENT DOCUMENTS

| 5,318,986 A * | 6/1994 | Hara et al. ..................... 514/456 |
| 2004/0013707 A1 * | 1/2004 | King et al. ..................... 424/439 |

FOREIGN PATENT DOCUMENTS
EP    0 629 350 A1    12/1994
(Continued)

OTHER PUBLICATIONS

Song et al, "Epigallocatechin Gallate Prevents Autoimmune Diabetes Induced by Multiple Low Doses of Streptozotocin in Mice", Arcives of Pharmacal Research (Seoul), vol. 26, No. 7, Jul. 2003, pp. 559-563.

(Continued)

*Primary Examiner* — Christopher R. Tate
*Assistant Examiner* — Roy Teller
(74) *Attorney, Agent, or Firm* — Nixon & Vanderhye P.C.

(57) ABSTRACT

The present invention describes a composition comprising EGCG and a protein hydrolysate.

20 Claims, No Drawings

FOREIGN PATENT DOCUMENTS

| | | |
|---|---|---|
| WO | WO 01/37850 A2 | 5/2001 |
| WO | WO 01/37850 A3 | 5/2001 |
| WO | WO 03/102195 A1 | 12/2003 |

OTHER PUBLICATIONS

Han, "Epigallocatechin gallate, a constituent of green tea, suppresses cytokine-induced pancreatic β-cell damage", Experimental and Molecular Medicine, vol. 35, No. 2, Apr. 30, 2003, pp. 136-139.

International Search Report mailed May 15, 2006 in PCT/EP2006/050623.

Seeram et al, "Catechin and Caffeine Content of Green Tea Dietary Supplements and Correlation with Antioxidant Capacity", J. Agric. Food Chem. 2006, 54, 1599-1603.

Morato et al, "Optimizationof Casein Hydrolysis for Obtaining High Contents of Small Peptides: Use of Subtilisin and Trypsin", Journal of Food Composition and Analysis (2000) 13, 843-857.

\* cited by examiner

COMPOSITIONS COMPRISING EPIGALLOCATECHIN GALLATE AND PROTEIN HYDROLYSATE

This application is the US national phase of international application PCT/EP2006/050623 filed 2 Feb. 2006 which designated the U.S. and claims benefit of EP 05100755.7, dated 3 Feb. 2005, the entire content of which is hereby incorporated by reference.

The present invention relates to novel compositions comprising epigallocatechin gallate (hereinafter EGCG).

Diabetes mellitus is a widespread chronic disease that hitherto has no cure. The incidence and prevalence of diabetes mellitus is increasing exponentially and it is among the most common metabolic disorders in developed and developing countries. Diabetes mellitus is a complex disease derived from multiple causative factors and characterized by impaired carbohydrate, protein and fat metabolism associated with a deficiency in insulin secretion and/or insulin resistance. This results in elevated fasting and postprandial serum glucose concentrations that lead to complications if left untreated. There are two major categories of the disease, insulin-dependent diabetes mellitus (IDDM, T1DM) and non-insulin-dependent diabetes mellitus (NIDDM, T2DM).

T1DM and T2DM diabetes are associated with hyperglycemia, hypercholesterolemia and hyperlipidemia. The absolute insulin deficiency and insensitivity to insulin in T1DM and T2DM, respectively, leads to a decrease in glucose utilization by the liver, muscle and the adipose tissue and to an increase in the blood glucose levels. Uncontrolled hyperglycemia is associated with increased and premature mortality due to an increased risk for microvascular and macrovascular diseases, including nephropathy, neuropathy, retinopathy, hypertension, stroke, and heart disease. Recent evidence showed that tight glycemic control is a major factor in the prevention of these complications in both T1DM and T2DM. Therefore, optimal glycemic control by drugs or therapeutic regimens is an important approach for the treatment of diabetes.

Therapy of T2DM initially involves dietary and lifestyle changes, when these measures fail to maintain adequate glycemic control the patients are treated with oral hypoglycemic agents and/or exogenous insulin. The current oral pharmacological agents for the treatment of T2DM include those that potentiate insulin secretion (sulphonylurea agents), those that improve the action of insulin in the liver (biguanide agents), insulin-sensitizing agents (thiazolidinediones) and agents which act to inhibit the uptake of glucose (α-glucosidase inhibitors). However, currently available agents generally fail to maintain adequate glycemic control in the long term due to progressive deterioration of hyperglycemia, resulting from progressive loss of pancreatic cell function. The proportion of patients able to maintain target glycemia levels decreases markedly over time necessitating the administration of additional/alternative pharmacological agents. Furthermore, the drugs may have unwanted side effects and are associated with high primary and secondary failure rates. Finally, the use of hypoglycemic drugs may be effective in controlling blood glucose levels, but may not prevent all the complications of diabetes. Thus, current methods of treatment for all types of diabetes mellitus fail to achieve the ideals of normoglycemia and the prevention of diabetic complications.

Therefore, although the therapies of choice in the treatment of T1DM and T2DM are based essentially on the administration of insulin and of oral hypoglycemic drugs, there is a need for a safe and effective nutritional supplement with minimal side effects for the treatment and prevention of diabetes.

Many patients are interested in alternative therapies which could minimize the side effects associated with high-dose of drugs and yield additive clinical benefits. Patients with diabetes mellitus have a special interest in treatment considered as "natural" with mild anti-diabetic effects and without major side effects, which can be used as adjuvant treatment. T2DM is a progressive and chronic disease, which usually is not recognized until significant damage has occurred to the pancreatic cells responsible for producing insulin (β-cells of islets of Langerhans). Therefore, there is an increasing interest in the development of a dietary supplement that may be used to prevent β-cell damage and thus, the progression to overt T2DM in people at risk especially in elderly who are at high risk for developing T2DM. Protection of pancreatic β-cells may be achieved by decreasing blood glucose and/or lipid levels as glucose and lipids exert damaging effects on β-cells. The reduction of blood glucose levels can be achieved via different mechanisms, for example by enhancing insulin sensitivity and/or by reducing hepatic glucose production. The reduction of blood lipid levels can also be achieved via different mechanisms, for example by enhancing lipid oxidation and/or lipid storage. Another possible strategy to protect pancreatic β-cells would be to decrease oxidative stress. Oxidative stress also causes β-cell damage with subsequent loss of insulin secretion and progression to overt T2DM.

Therefore, T2DM is a complicated disease resulting from coexisting defects at multiple organ sites: resistance to insulin action in muscle and adipose tissues, defective pancreatic insulin secretion, unrestrained hepatic glucose production. Those defects are often associated with lipid abnormalities and endothelial dysfunction. Given the multiple pathophysiological lesions in T2DM, combination therapy is an attractive approach to its management.

In accordance with the present invention it has surprisingly been found that a composition comprising EGCG and certain peptides preserves the morphology of islets of Langerhans of the pancreas and prevents β-cell damage.

The present invention in one aspect relates to novel compositions comprising epigallocatechin gallate and a protein hydrolysate (or peptides or polypeptides) and, optionally, one or more compounds selected from ligustilide or other phthalides or herbal extracts containing ligustilide or other phthalides, coenzyme Q-10, resveratrol, pantethine or a metabolite thereof, phytanic acid, lipoic acid, and policosanol. In another aspect, the present invention relates to nutraceutical compositions containing the aforesaid component as active ingredients for the treatment or prevention of diabetes mellitus, or other conditions associated with impaired glucose tolerance such as syndrome X and obesity. In still another aspect the present invention relates to the use of such compositions as a nutritional supplement for the said treatment or prevention, e.g., as an additive to a multi-vitamin preparations comprising vitamins and minerals which are essential for the maintenance of normal metabolic function but are not synthesized in the body. In still another aspect, the invention relates to a method for the treatment of both type 1 and 2 diabetes mellitus (hereinafter: T1DM and T2DM), and for the prevention of T2DM in those individuals with pre-diabetes, or impaired glucose tolerance (IGT) or obesity which comprises administering to a subject in need of such treatment EGCG and a protein hydrolysate and, optionally, one or more compounds selected from ligustilide or other phthalides or herbal extracts containing ligustilide or other phthalides, coenzyme Q-10, resveratrol, pantethine or a metabolite thereof, phytanic acid, lipoic acid, and policosanol. The latter compounds have different mechanism of action on glucose metabolism and insulin sensitivity thus, providing additive and/or synergetic effects in the treatment of diabetes mellitus.

The term nutraceutical as used herein denotes the usefulness in both the nutritional and pharmaceutical field of application. Thus, the novel nutraceutical compositions can find use as supplement to food and beverages, and as pharmaceutical formulations for enteral or parenteral application which may be solid formulations such as capsules or tablets, or liquid formulations, such as solutions or suspensions. As will be evident from the foregoing, the term nutraceutical composition also comprises food and beverages containing EGCG and a protein hydrolysate, peptides or polypeptides, and optionally one or more components selected from ligustilide or other phthalides or herbal extracts containing ligustilide or other phthalides, coenzyme Q-10, resveratrol, pantethine or a metabolite thereof, phytanic acid, lipoic acid, and policosanol as well as supplement compositions, for example dietary supplements, containing the aforesaid active ingredients.

The term dietary supplement as used herein denotes a product taken by mouth that contains a "dietary ingredient" intended to supplement the diet. The "dietary ingredients" in these products may include: vitamins, minerals, herbs or other botanicals, amino acids, and substances such as enzymes, organ tissues, glandulars, and metabolites. Dietary supplements can also be extracts or concentrates, and may be found in many forms such as tablets, capsules, softgels, gelcaps, liquids, or powders. They can also be in other forms, such as a bar, but if they are, information on the label of the dietary supplement will in general not represent the product as a conventional food or a sole item of a meal or diet.

Protein hydrolysate is preferably combined with EGCG, but peptides or polypeptides can also be used in the present invention. A "peptide" or "oligopeptide" is defined herein as a chain of at least two amino acids that are linked through peptide bonds. The terms "peptide" and "oligopeptide" are considered synonymous (as is commonly recognized) and each term can be used interchangeably as the context requires.

A "polypeptide" is defined herein as a chain comprising of more than 30 amino acid residues. All (oligo)peptide and polypeptide formulas or sequences herein are written from left to right in the direction from amino-terminus to carboxyterminus, in accordance with common practice.

Protein hydrolysates for use in the present invention are particularly those wherein the molar fraction of peptides (%) carrying a carboxy terminal proline is more than two times the molar fraction (%) of proline in the protein substrate used to generate the hydrolysate. Such hydrolysates are disclosed and claimed in the international application WO 02/45523 and WO 02/45524 the contents of which are included herein for reference purposes. Thus, in one aspect, the present invention is concerned with compositions for the treatment or prevention of type 2 diabetes mellitus (T2DM) in those individuals with pre-diabetes, or impaired glucose tolerance (IGT), or obesity, or established type 2 diabetes mellitus comprising EGCG and a protein hydrolysate preferably containing peptides, wherein the molar fraction of peptides (%) carrying a carboxy terminal proline is more than two times the molar fraction (%) of proline in the protein substrate used to generate the hydrolysate.

As stated above, the effects of the composition of the present invention were much greater than the expected effects exerted by the active ingredients, viz., EGCG, polypeptides, or protein hydrolysates, alone. Thus, the compositions of the present invention synergistically protect pancreatic β-cells and maintain the morphology of pancreatic islets of Langerhans and can thus be used to prevent or treat both T1DM and T2DM, and for the prevention of T2DM in those individuals with pre-diabetes, impaired glucose tolerance (IGT), or obesity.

The combinations of the present invention may optionally contain one or more components selected from ligustilide or other phthalides or herbal extracts containing ligustilide or other phthalides, coenzyme Q-10, resveratrol, pantethine or a metabolite thereof, phytanic acid, lipoic acid, and policosanol, which individually exert different mechanisms of action and are effective in achieving and maintaining target blood glucose levels in diabetic patients.

The combinations of the active ingredients identified above have been conceived because of their different actions, to take advantage of additive/synergistic and multiorgan effects. Owing to distinct mechanisms of action of the individual active ingredients the combinations not only improve glycemic control, but also result in lower drug dosing in some settings and minimize adverse effects. Because of their distinct mechanisms and sites of action, the specific combinations of dietary supplements discussed above also take advantage of additive/synergistic effects to achieve a degree of glucose lowering greater than single agents can accomplish. Thus, although the therapies of choice in the therapeutic treatment of T1DM and T2DM is based essentially on the administration of insulin and of oral hypoglycemic drugs, appropriate nutritional therapy is also of major importance for the successful treatment of diabetics.

The function of each of the active ingredients of the nutraceutical compositions of the present invention is described below:

EGCG: Epigallocatechin gallate (EGCG) is the major catechin found in green tea. In rats green tea catechins dose-dependently suppressed the increase in glucose and insulin levels in plasma after a starch or a sucrose rich meal. Furthermore, EGCG enhances glucose tolerance in a mouse model of T2DM.

Protein hydrolysates: When protein hydrolysates are given to humans concomitantly to a glucose load, a potentiation of the insulin response (insulin secretion) can be observed. This may lead to faster uptake of circulating blood glucose into insulin-responsive tissues like adipose tissue and skeletal muscle resulting in a faster reduction of blood glucose levels.

Combination of EGCG and protein hydrolysates: A composition comprising EGCG and protein hydrolysates surprisingly results in a pronounced preservation of pancreatic β-cells and maintains the morphology of pancreatic islets of Langerhans. The protection of insulin-secreting structures in the pancreas is especially beneficial for humans with T2DM and for the prevention of T2DM in those individuals with pre-diabetes, or impaired glucose tolerance (IGT), or obesity.

Ligustilide: In a mouse model of T2DM oral treatment with ligustilide enhances glucose tolerance and exerts insulin-sensitizing effects. As mentioned above, one typical feature of T2DM is the resistance to insulin-action in adipose tissue and skeletal muscle. Thus, by enhancing the action of insulin on its target tissues ligustilide may be beneficial for treatment of humans with T2DM and for the prevention of T2DM in those individuals with pre-diabetes, or impaired glucose tolerance (IGT), or obesity.

Coenzyme Q-10: Coenzyme Q-10, (6-Decaprenyl-2,3-dimethoxy-5-methyl-1,4-benzoquinone) is a fat soluble quinone with a structure similar to vitamin K. The health beneficial effects of Coenzyme Q10 (CoQ10) have been associated with its two main biochemical functions. CoQ10 is an essential cofactor of the mitochondrial electron transport chain, which is coupled to synthesis of adenosine triphosphate (ATP). Therefore, it acts as a catalyst in the biochemical pathway that leads to cellular energy production. This bioenergic effect of CoQ10 is of particular importance in cells with high metabolic demands such as cardiac myocytes. Moreover, CoQ10 is an important antioxidant in both the mitochondria and lipid membranes. CoQ10 exerts a sparing effect on vitamin E and has membrane stabilizing properties. Several studies showed that LDL oxidation was reduced after CoQ10 supplementation. Thus CoQ10 may improve energy metabolism and protect against oxidative stress in diabetes and cardiovascular diseases.

Resveratrol: Resveratrol (3,4',5-trihydroxy-trans-stilbene), a phytoalexin found in grape skins, peanuts, and red wine, has been reported to exhibit a wide range of biological and pharmacological properties. Dietary resveratrol acts as an antioxidant, promotes nitric oxide production, inhibits platelet aggregation, and increases high-density lipoprotein cholesterol and thereby serves as a cardioprotective agent (the so-called "French paradox"). Furthermore, resveratrol functions as a co-repressor of PPAR-γ and as an activator of sirtuin and can thereby directly influence obesity and T2DM as well as longevity, respectively. Thus, resveratrol helps subjects with T2DM, impaired glucose tolerance (IGT), or obesity to reduce or to prevent the negative effects caused by high blood levels of glucose or lipids.

Pantethine: In human studies oral administration of pantethine resulted in a progressive decrease in total cholesterol, triglycerides, low density lipoprotein (LDL) cholesterol and an increase in high density lipoprotein (HDL) cholesterol. Thus, resulting in a more favorable Cholesterol/HDL ratio which reduces cardiovascular risk. Diabetes mellitus is associated with a 3- to 4-fold increase in risk of coronary artery disease. T2DM adversely affects the plasma lipid profile, increasing levels of atherogenic lipids such as low density lipoproteins (LDL) and very low density lipoproteins (VLDL), but decreasing levels of high density lipoprotein (HDL), an antiatherogenic lipid. Atherosclerotic manifestations are not only common in individuals with diabetes but also result in significant long-term complications. Therefore, the oral supplementation with pantethine helps diabetes patients to normalize their lipid values reducing the risk of coronary heart disease and of thrombotic events. Instead of or in addition to pantethine, metabolites of pantethine such as cysteamine and pantothenic acid may find use in accordance with the invention.

Lipoic acid: Lipoic acid (1,2-dithiolane-3-pentaenoic acid) plays an essential role in mitochondrial-specific pathways that generate energy from glucose and may potentially influence the rate of glucose oxidation. Lipoic acid stimulates glucose transport in both muscle and adipose cells in culture. Moreover, administration of lipoic acid also raised basal and insulin-stimulated glucose uptake by skeletal muscles of animals with T2DM. Furthermore, lipoic acid improves glucose disposal in patients with T2DM and may be incorporated in a nutraceutical composition of the present invention in order to prevent and/or treat the diabetes related complications and as agent with insulin sensitizing activity.

Phytanic acid: Phytanic acid (3,7,11,15-tetramethylhexadecanoic acid) at concentrations ranging from about 10 to about 100 µM enhances uptake of glucose in rat primary hepatocytes. Compared to the specific PPAR-γ agonist such as ciglitazone, phytanic acid exerts only minor effects on the differentiation of pre-adipocyte cells into mature adipocytes. Therefore, intake of phytanic acid helps to improve insulin sensitivity and may act as a preventative measure against T2DM through activation of PPARs and RXR.

Policosanol: Policosanol is a mixture of primary aliphatic alcohols isolated and purified from plant waxes, mainly sugar cane. The aliphatic alcohol of the mixture is a $CH_3$—$(CH_2)_n$—$CH_2OH$ alcohol with chain length varying from 18 to 40 carbon atoms. Typical aliphatic alcohols of the mixture are octacosanol, hexacosanol, heptacosanol, triacontanol and dotriacontanol. Policosanol has been shown to lower cholesterol in animal models, healthy volunteers, and patients with type II hypercholesterolemia. Therefore, it is useful in the dyslipidemia associated with type 2 diabetes mellitus.

A multi-vitamin and mineral supplement may be added to the nutraceutical compositions of the present invention to obtain an adequate amount of an essential nutrient missing in some diets. The multi-vitamin and mineral supplement may also be useful for disease prevention and protection against nutritional losses and deficiencies due to lifestyle patterns and common inadequate dietary patterns sometimes observed in diabetes. Moreover, oxidant stress has been implicated in the development of insulin resistance. Reactive oxygen species may impair insulin stimulated glucose uptake by disturbing the insulin receptor signaling cascade. The control of oxidant stress with antioxidants such as α-tocopherol (vitamin E) ascorbic acid (vitamin C) may be of value in the treatment of diabetes. Therefore, the intake of a multi-vitamin supplement may be added to the above mentioned active substances to maintain a good balanced nutrition.

In a preferred aspect of the invention, the nutraceutical composition of the present invention contains EGCG and a protein hydrolysate as defined earlier. EGCG suitably is present in the composition according to the invention in an amount to provide a daily dosage from about 0.3 mg per kg body weight to about 30 mg per kg body weight of the subject to which it is to be administered. A food or beverage suitably contains about 5 mg per serving to about 500 mg per serving of EGCG. If the nutraceutical composition is a pharmaceutical formulation such formulation may contain EGCG in an amount from about 10 mg to about 500 mg per dosage unit, e.g., per capsule or tablet, or from about 20 mg per daily dose to about 2000 mg per daily dose of a liquid formulation. The protein hydrolysate is suitably present in the composition according to the invention in an amount to provide a daily dosage from about 0.01 mg per kg body weight to about 3 g per kg body weight of the subject to which it is to be administered. A food or beverage suitably contains about 0.1 g per serving to about 100 g per serving of protein hydrolysates. If the nutraceutical composition is a pharmaceutical formulation such formulation may contain protein hydrolysates in an amount from about 0.01 mg to about 500 mg per dosage unit, e.g., per capsule or tablet, or from about 0.7 g per daily dose to about 210 g per daily dose of a liquid formulation. Suitable hydrolysates are for example hydrolysates produced from whole milk, skimmed milk, acid casein, rennet casein, acid whey products or cheese whey products. Other suitable protein sources are collagen-based animal proteins such as gelatin as well as bones or fishbones containing residual meat, interesting substrates for the enzyme. Moreover, vegetable substrates like wheat gluten, milled barley and protein fractions obtained from, for example, soy, rice or corn are suitable substrates.

The protein hydrolysate is preferably a protein hydrolysate which comprises peptides, wherein the molar fraction of the peptides (%) carrying a carboxy terminal proline is more than two times higher than the molar fraction (%) of proline in the protein substrate used to generate the hydrolysate. The protein hydrolysate comprises preferably peptides wherein the molar fraction of peptides carrying a carboxyterminal proline is from 8 to 70%, preferably 15 to 70%, more preferably 30 to 70%. According to the present invention the protein hydrolysate used has preferably a degree of hydrolysis (DH) of between 10 and 60, more preferably a DH of between 15 and 50 and most preferably a DH of between 20 and 40.

The Degree of Hydrolysis (DH) as obtained during incubation with the various protolytic mixtures was monitored using a rapid OPA test (Nielsen, P. M.; Petersen, D.; Dambmann, C. Improved method for determining food protein degree of hydrolysis. *Journal of Food Science* 2001, 66, 642-646).

The protein hydrolysate is furthermore preferably
- a whey hydrolysate which comprises peptides wherein the molar fraction of peptides carrying a carboxy terminal proline is at least 8%, preferably at least 15%, more preferably from 30 to 70% and/or
- a casein hydrolysate which comprises peptides wherein the molar fraction of peptide carrying a carboxy terminal proline is at least 25%, preferably at least 30% and more preferably less than 70% and/or
- a soy hydrolysate which comprises peptides wherein the molar fraction of peptide carrying a carboxy terminal proline is at least 20%, preferably from 30 to 70% and/or
- a gluten hydrolysate which comprises peptides wherein the molar fraction of peptide carrying a carboxy terminal proline is at least 20%, preferably at least 30%, advantageously less than 70% and/or
- a barley hydrolysate which comprises peptides wherein the molar fraction of peptide carrying a carboxy terminal proline is at least 20%, preferably at least 30%, advantageously less than 70%.

Furthermore is preferred that the protein hydrolysate having a high content of peptides with a terminal proline is a protein hydrolysate which is rich in tripeptides, whereby the tripeptides are rich in proline at one end of the peptide.

The protein hydrolysates for use in the compositions of the present invention are well-known in the prior art. The whey, casein, soy, gluten and barley hydrolysates as particularly specified above and their preparation is known from WO 02/45523 and WO 02/45524 which are incorporated herein by reference. The protein hydrolysate is preferably a protein hydrolysate which comprises peptides, wherein the molar fraction of peptides (%) carrying a carboxy terminal proline is more than two times higher than the molar fraction (%) of proline in the protein substrate used to generate the hydrolysate, and such a protein hydrolysate is also known from these documents. Reference is made to these documents in particular regarding the preparation of the protein hydrolysates which is described in the documents in detail.

Protein hydrolysates which are rich in tripeptides, whereby the tripeptides are rich in proline at one end of the peptide, are known from WO 03/102195, and this document is also incorporated herein by reference. It is referred to WO 03/102195 in particular regarding the process for producing the protein hydrolysates which are rich in tripeptides, whereby the tripeptides are rich in proline at one end of the peptide, and regarding further preferred protein hydrolysates. The preferred protein hydrolysates of the present invention are also the preferred protein hydrolysates disclosed in WO 03/102195.

Protein hydrolysates which can be used for the present invention can also be prepared with the novel proteolytic enzymes disclosed in WO 02/068623, and this document is also incorporated herein by reference regarding preferred production methods of protein hydrolysates which can be used for the cosmetic compositions of the present invention.

Thus, the present invention provides compositions containing a protein hydrolysate with a high content of terminal proline which is known from WO 03/102195, WO 02/45523 and/or WO 02/45524.

Particularly preferred are protein hydrolysates which are rich in tripeptides, whereby the tripeptides are rich in proline at one end of the peptide, wherein the peptide has a carboxy terminal proline as disclosed in WO 03/102195. These hydrolysates may optionally also comprise dipeptides. More preferred is a protein hydrolysate which is rich in tripeptides, wherein the tripeptides are rich in proline at one end of the peptide, preferably the carboxyl end of the peptide, wherein at least 20 molar %, more preferably at least 25 molar %, still more preferably at least 30 molar % of the peptides having a molecular weight of 200 to 2000 Dalton is present in the hydrolysate as tripeptide. Preferred is also a protein hydrolysate as defined above, wherein preferably at least 20%, more preferably at least 30%, still more preferably at least 40% of the proline present in the starting protein is present in the tripeptides. Preferred are also the protein hydrolysates as defined above, wherein at least 30% of the tripeptides or preferably at least 35% of the tripeptides have a carboxy terminal proline. Preferred are also the protein hydrolysates as defined above, wherein at least 70 molar % of the peptides, more preferably at least 75 molar % of the peptides, contain 2 to 7 amino acid residues (dipeptide to heptapeptide). Other preferred protein hydrolysates are known from WO 03/102195.

Referring now to the whey, casein, soy, gluten and barley hydrolysates as particularly specified above, and the protein hydrolysate which is a protein hydrolysate which comprises peptides, wherein the molar fraction of peptides (%) carrying a carboxy terminal proline is more than two times higher than the molar fraction (%) of proline in the protein substrate used to generate the hydrolysate and which are disclosed in WO 02/45523 and in WO 02/45524, the following preferred embodiments should be noted.

Preferably, the protein hydrolysate as defined above comprises peptides, wherein the molar fraction of peptides (%) carrying a carboxy terminal proline is at least two times, more preferably at least three times, the molar fraction (%) of proline in the protein substrate used to produce the hydrolysates. Preferably, the average length of the peptides in the protein hydrolysates is from 3 to 9 amino acids. Preferred hydrolysates are a whey hydrolysate which comprises peptides wherein the molar fraction of peptides carrying a carboxy terminal proline is at least 8%, preferably at least 15%, more preferably from 30 to 70%, a casein hydrolysate which comprises peptides wherein the molar fraction of peptide carrying a carboxy terminal proline is at least 25%, preferably from 30 to 70%, and a soy hydrolysate which comprises peptides wherein the molar fraction of peptides carrying a carboxy terminal proline is at least 20%, preferably from 30 to 70%. Preferred are protein hydrolysates, wherein at least 10% of the protein substrate is hydrolyzed, preferably wherein from 20 to 90% of the protein substrate is hydrolyzed. By peptides or peptide fragments it is preferably meant peptides with molecular masses from 400 to 2000 Dalton. These peptides can be analyzed according to the LC/MC analysis as described in WO 02/45523.

In general in the production of the protein hydrolysates the protein substrate is substantially hydrolyzed, advantageously for at least 50%. Preferably at least 10% of the protein substrate is converted into peptides having molecular masses from 400 to 2000 Dalton. More preferably from 20 to 90% and even more preferably from 30 to 80% of the protein substrate is converted into such peptides.

In case a peptide or a peptide mixture is used in the present invention, which is combined with EGCG, preferably 20 to 100 molar % of the peptides has a molecular mass of from 400 to 2000 Dalton, more preferably 40 to 100 molar % has a molecular mass of from 400 to 2000 Dalton. Such peptide or peptide mixture has equivalent activity as a protein hydrolysate in the present invention. So throughout the present specification the wording "protein hydrolysate" or "hydrolysate" can be replaced by the wording "peptide or peptide mixture". The peptide or peptide mixture can for example be isolated or purified from a hydrolysate or produced via chemical synthesis.

In one embodiment, a protein substrate may be incubated with an enzyme mixture comprising an isolated, purified proline-specific endoprotease, a serine endoprotease or a metallo endoprotease and a carboxypeptidase to produce a protein hydrolysate enriched in peptide fragments having a carboxy terminal proline as disclosed in WO 02/45523.

The enzyme mixture of WO 02/45523 which is preferably used in the present invention is characterized in that it contains at least one endoprotease for example a serine protease or a metallo endoprotease in conjunction with a proline-specific endoprotease (E. C. 3.4.21.26) to provide a primary hydrolysate. More specifically, an isolated, purified proline-specific endoprotease and a serine protease or metallo protease enzyme mixture capable of producing a protein hydrolysate comprising peptide fragments, wherein at least 8%, preferably at least 15%, more preferably from 30 to 70% of said peptide fragments have a carboxy terminal proline as disclosed in WO 02/45523 is used.

Preferred is also a protein hydrolysate enriched with a relatively high content of peptides having proline as the carboxy terminal amino acid residue. Such enriched hydrolysates may comprise at least 8%, preferably at least 15%, more preferably from 30 to 70% peptide fragments having a carboxy terminal proline residue. These protein hydrolysates can be obtained by enzyme preparations which are capable of generating peptides bearing proline residues at carboxy termini, which are disclosed in WO 02/45523.

Most preferred are protein hydrolysates which can be obtained by a process corresponding to the process of example 1 of WO 02/45523, using a suitable substrate. Preferred are also mixtures of the protein hydrolysates disclosed in WO 02/45523 and in WO 03/102195.

Substrates for hydrolysis by an enzyme mixture include whole milk, skimmed milk, acid casein, rennet casein, acid whey products or cheese whey products. The *Aspergillus* derived proline-specific endoprotease does not only cleave at the carboxy terminal side of proline residues but also at the carboxy terminal side of hydroxyproline residues which makes other, collagen-based animal proteins such as gelatin as well as bones or fishbones containing residual meat, interesting substrates for the enzyme. Moreover, vegetable substrates like wheat gluten, milled barley and protein fractions obtained from, for example, soy, rice or corn are suitable substrates. Milk protein hydrolysates produced according to WO 02/45523 may be used with or without additional filtration or purification steps.

In another preferred aspect of the invention, the nutraceutical composition of the present invention further contains ligustilide or other phthalides or herbal extracts containing ligustilide or other phthalides. If ligustilide or other phthalides or herbal extracts containing ligustilide or other phthalides are present in the nutraceutical composition according to the invention their amounts may be such to provide a daily dosage from about 0.1 mg per kg body weight to about 100 mg per kg body weight of the subject to which it is to be administered. A food or beverage suitably contains about 1 mg per serving to about 500 mg per serving of ligustilide or other phthalides. If the nutraceutical composition is a pharmaceutical formulation such formulation may contain ligustilide or other phthalides or herbal extracts containing ligustilide or other phthalides in an amount from about 1 mg to about 500 mg per dosage unit, e.g., per capsule or tablet, or from about 2 mg per daily dose to about 1000 mg per daily dose of a liquid formulation.

In another aspect of the invention, the nutraceutical composition of the present invention further contains Coenzyme Q-10. If Coenzyme Q-10 is present in the nutraceutical composition according to the invention its amount may be such to provide a daily dosage from about 0.01 mg per kg body weight to about 30 mg per kg body weight of the subject to which it is to be administered. A food or beverage suitably contains about 1 mg per serving to about 400 mg per serving of CoQ10. If the nutraceutical composition is a pharmaceutical formulation such formulation may contain CoQ10 in an amount from about 1 mg to about 500 mg per dosage unit, e.g., per capsule or tablet, or from about 1 mg per daily dose to about 2000 mg per daily dose of a liquid formulation.

In yet another aspect of the invention, the nutraceutical composition of the present invention further contains resveratrol. The amount of resveratrol in the composition may be such to provide a daily dosage from about 0.01 mg per kg body weight to about 50 mg per kg body weight of the subject to which it is to be administered. A food or beverage suitably contains about 1 mg per serving to about 500 mg per serving of resveratrol. If the nutraceutical composition is a pharmaceutical formulation such formulation may contain resveratrol in an amount from about 1 mg to about 1000 mg per dosage unit, e.g., per capsule or tablet, or from about 1 mg per daily dose to about 1000 mg per daily dose of a liquid formulation.

If pantethine is present in the nutraceutical composition according to the invention its amount may be such to provide a daily dosage from about 1 mg per kg body weight to about 50 mg per kg body weight of the subject to which it is to be administered. A food or beverage suitably contains about 20 mg per serving to about 800 mg per serving of pantethine. If the nutraceutical composition is a pharmaceutical formulation such formulation may contain pantethine in an amount from about 20 mg to about 1000 mg per dosage unit, e.g., per capsule or tablet, or from about 70 mg per daily dose to about 3500 mg per daily dose of a liquid formulation.

If phytanic acid is present in the nutraceutical composition according to the invention its amount may be such to provide a daily dosage from about 1 mg per kg body weight to about 100 mg per kg body weight of the subject to which it is to be administered. A food or beverage suitably contains about 20 mg per serving to about 2000 mg per serving of phytanic acid. If the nutraceutical composition is a pharmaceutical formulation such formulation may contain phytanic acid in an amount from about 30 mg to about 500 mg per dosage unit, e.g., per capsule or tablet, or from about 70 mg per daily dose to about 7000 mg per daily dose of a liquid formulation. Phytanic acid may also be used in the form of a biologically equivalent derivative thereof, such as an ester, e.g. the methyl or ethyl ester.

If lipoic acid is present in the nutraceutical composition according to the invention its amount may be such to provide a daily dosage from about 0.3 mg per kg body weight to about 30 mg per kg body weight of the subject to which it is to be administered. A food or beverage suitably contains about 5 mg per serving to about 500 mg per serving of lipoic acid. If the nutraceutical composition is a pharmaceutical formulation such formulation may contain lipoic acid in an amount from about 5 mg to about 800 mg per dosage unit, e.g., per capsule or tablet, or from about 5 mg per daily dose to about 2000 mg per daily dose of a liquid formulation.

If policosanol is present in the nutraceutical composition according to the invention its amount may be such to provide a daily dosage from about 0.002 mg per kg body weight to about 1.5 mg per kg body weight of the subject to which it is to be administered. A food or beverage suitably contains about 0.1 mg per serving to about 20 mg per serving of policosanol. If the nutraceutical composition is a pharmaceutical formulation such formulation may contain policosanol in an amount from about 0.1 mg to about 30 mg per dosage unit, e.g., per capsule or tablet, or from about 0.1 mg per daily dose to about 100 mg per daily dose of a liquid formulation.

Preferred nutraceutical compositions of the present invention comprise EGCG and protein hydrolysates as the sole active ingredients. Further preferred are compositions comprising optionally one or more components selected from ligustilide or other phthalides or herbal extracts containing ligustilide or other phthalides, coenzyme Q-10, resveratrol, pantethine or a metabolite thereof, phytanic acid, lipoic acid; more particularly compositions comprising EGCG, protein hydrolysates, ligustilide or other phthalides or herbal extracts containing ligustilide or other phthalides, Coenzyme Q-10, and resveratrol; especially the combinations of EGCG, protein hydrolysates, ligustilide or other phthalides or herbal extracts containing ligustilide or other phthalides;

EGCG, protein hydrolysates and Coenzyme Q-10;

EGCG, protein hydrolysates and resveratrol;

EGCG, protein hydrolysates, ligustilide or other phthalides or herbal extracts containing ligustilide or other phthalides, and Coenzyme Q-10;

EGCG, protein hydrolysates, ligustilide or other phthalides or herbal extracts containing ligustilide or other phthalides and resveratrol;

Most preferred are the combinations of EGCG and protein hydrolysates and, optionally, ligustilide and/or Coenzyme Q-10.

Dosage Ranges (for a 70 kg Person)
EGCG: 20-2100 mg/day
Protein hydrolysates: 0.07-210 g/day
Ligustilide or other phthalides: 1-1000 mg/day
Coenzyme Q-10:1-2100 mg/day
Resveratrol: 1-1000 mg/day
Pantethine: 70-3500 mg/day
Phytanic acid: 70-7000 mg/day
Lipoic acid: 20-2100 mg/day
Policosanol: 0.15-100 mg/day As stated above food or beverage are suitably used for administration of the present invention. Beverages which can be used for the supplementation of the composition of the invention can be in the form of beverage, such as sports drinks, energy drinks or other soft drinks, or any other suitable nutrient preparation.

A sports drink is a beverage which is supposed to rehydrate athletes, as well as restoring electrolytes, sugar, and other nutrients. Sports drinks are usually isotonic, meaning they contain the same proportions of nutrients as found in the human body. (Source: http://en.wikipedia.org/wiki/Sports_drink)

Energy drinks are beverages which contain (legal) stimulants, vitamins (especially B vitamins) and minerals with the intent to give the user a burst of energy. Common ingredients include caffeine, guarana (caffeine from the Guarana plant), taurine, various forms of ginseng, maltodextrin, inositol, carnitine, creatine, glucuronolactone and *ginkgo biloba*. Some may contain high levels of sugar, or glucose. Many such beverages are flavored and/or colored. (Source: http://en.wikipedia.org/wiki/Energy_drink)

A soft drink is a drink that does not contain alcohol, as opposed to hard drinks, that do. In general, the term is used only for cold beverages. Hot chocolate, tea, and coffee are not considered soft drinks. The term originally referred exclusively to carbonated drinks, and is still commonly used in this manner. (Source: http://en.wikipedia.org/wiki/Soft_drink)

EXAMPLE 1

Diets containing EGCG, or protein hydrolysate, or the combination of EGCG and protein hydrolysate, or placebo were administered to db/db mice (6 weeks old). The db/db mouse model of severe type 2 diabetes mellitus is well established and commonly used to assess the antidiabetic properties of nutritional or pharmaceutical interventions. Furthermore, the animals are characterized by a progressive loss of pancreatic function and pathological changes of pancreatic histology and morphology. The pancreatic damage occurring in db/db mice is the consequence of high blood glucose and lipid levels. After 10 weeks of administration of the respective diets pancreata of all mice were removed and assessed for pathologically changed islets of Langerhans. Pathologically changed islets displayed loss of definition of islet boundary and displacement of exocrine tissue (cells, ducts) into the islet tissue. The results are shown in Table 1.

TABLE 1

Pathologically changed islets of Langerhans of pancreata of db/db mice (n = 9 per group). Pancreata were removed after 10 weeks of feeding diets containing placebo, EGCG, protein hydrolysate, or the combination of EGCG and protein hydrolysate. Results are expressed as means ± SEM.

| Diet containing | Pathological islets (in % of total islets) |
|---|---|
| Placebo | 58.8 ± 2.3 |
| EGCG | 36.5 ± 4.1 |
| Protein hydrolysate [1] | 62.0 ± 3.3 |
| EGCG + protein hydrolysate [1] | 20.6 ± 6.3 |

[1] Protein hydrolysate obtained from casein by hydrolysis with tripeptidylpeptidase according to Examples 1 and 2 of WO 03/102195.

In db/db mice consuming a diet containing EGCG the pancreas contained less pathologically changed islets of Langerhans compared to placebo. Consumption of a diet containing protein hydrolysate did not result in changed pancreatic content of pathological islets. However, the combination of EGCG and protein hydrolysate decreased the number of pathologically changed islets to a much greater extent than expected from the effects of the two dietary ingredients alone. Thus, the combination of EGCG and protein hydrolysate synergistically protects pancreatic islets of Langerhans from damage exerted by high blood glucose and lipid levels and is therefore beneficial for the prevention or treatment of both T1DM and T2DM, and for the prevention of T2DM in those individuals with pre-diabetes, impaired glucose tolerance (IGT), or obesity.

A. Pharmaceutical compositions may be prepared by conventional formulation procedures using the ingredients specified below:

EXAMPLE 2

Soft Gelatin Capsule
Soft gelatin capsules are prepared by conventional procedures using ingredients specified below:
Active ingredients: EGCG 150 mg, protein hydrolysates 300 mg, Ligustilide 50 mg
Other ingredients: glycerol, water, gelatin, vegetable oil

EXAMPLE 3

Hard Gelatin Capsule

Hard gelatin capsules are prepared by conventional procedures using ingredients specified below:
Active ingredients: EGCG 300 mg, protein hydrolysates 700 mg, Ligustilide 100 mg
Other ingredients:
Fillers: lactose or cellulose or cellulose derivatives q.s
Lubricant: magnesium state if necessary (0.5%)

EXAMPLE 4

Tablet

Tablets are prepared by conventional procedures using ingredients specified below:
Active ingredients: EGCG 100 mg, protein hydrolysates 400 mg, Ligustilide 30 mg
Other ingredients: microcrystalline cellulose, silicone dioxide ($SiO_2$), magnesium stearate, crosscarmellose sodium.

B. Food items may be prepared by conventional procedures using ingredients specified below:

EXAMPLE 5A

Soft Drink with 30% Juice
Typical serving: 240 ml
Active ingredients:

EGCG and protein hydrolysates and optionally one or more components selected from ligustilide and other phthalides, Coenzyme Q-10, resveratrol, pantethine, phytanic acid and lipoic acid are incorporated in this food item:
EGCG: 5-500 mg/per serving
Protein hydrolysates: 1.5-20 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving
I. A Soft Drink Compound is Prepared from the Following Ingredients:

Juice Concentrates and Water Soluble Flavors

| | [g] |
|---|---|
| 1.1 Orange concentrate | |
| 60.3° Brix, 5.15% acidity | 657.99 |
| Lemon concentrate | |
| 43.5° Brix, 32.7% acidity | 95.96 |
| Orange flavor, water soluble | 13.43 |
| Apricot flavor, water soluble | 6.71 |
| Water | 26.46 |
| 1.2 Color | |
| β-Carotene 10% CWS | 0.89 |
| Water | 67.65 |
| 1.3 Acid and Antioxidant | |
| Ascorbic acid | 4.11 |
| Citric acid anhydrous | 0.69 |
| Water | 43.18 |

-continued

| | [g] |
|---|---|
| 1.4 Stabilizers | |
| Pectin | 0.20 |
| Sodium benzoate | 2.74 |
| Water | 65.60 |
| 1.5 Oil soluble flavors | |
| Orange flavor, oil soluble | 0.34 |
| Orange oil distilled | 0.34 |

1.6 Active Ingredients

Active ingredients (this means the active ingredient mentioned above: EGCG and protein hydrolysates and optionally one or more components selected from ligustilide or other phthalides or herbal extracts containing ligustilide or other phthalides, Coenzyme Q-10, resveratrol, pantethine, lipoic acid, policosanol and/or phytanic acid) in the concentrations mentioned above.

Fruit juice concentrates and water soluble flavors are mixed without incorporation of air. The color is dissolved in deionized water. Ascorbic acid and citric acid is dissolved in water. Sodium benzoate is dissolved in water. The pectin is added under stirring and dissolved while boiling. The solution is cooled down. Orange oil and oil soluble flavors are premixed. The active ingredients as mentioned under 1.6 are dry mixed and then stirred preferably into the fruit juice concentrate mixture (1.1).

In order to prepare the soft drink compound all parts 3.1.1 to 3.1.6 are mixed together before homogenizing using a Turrax and then a high-pressure homogenizer ($p_1$=200 bar, $p_2$=50 bar).

II. A Bottling Syrup is Prepared from the Following ingredients:

| | [g] |
|---|---|
| Softdrink compound | 74.50 |
| Water | 50.00 |
| Sugar syrup 60° Brix | 150.00 |

The ingredients of the bottling syrup are mixed together. The bottling syrup is diluted with water to 1 l of ready to drink beverage.

Variations:

Instead of using sodium benzoate, the beverage may be pasteurized. The beverage may also be carbonized.

EXAMPLE 5B

A beverage can be made using the concept of a sport or energy drink. A drink based on the energy or sports drink concept can contain for example:
2-50 g hydrolysate, 10-200 mg EGCG, 10-50 g sugars (such as fructose, saccharose, glucose, maltodextrin), Vitamins such as B and C, for example 1-30 mg B vitamins (B1, B2, B5) and 10-700 mg vitamin C, and 100-600 mg minerals (such as NaCl, Mg). These ingredients (in general 20-100 g) are mixed with 500 ml water.

EXAMPLE 6

Five Cereal Bread
Typical serving: 50 g
Active ingredients:

EGCG and protein hydrolysates and optionally one or more components selected from ligustilide and other phthalides, Coenzyme Q-10, resveratrol, pantethine, phytanic acid and lipoic acid are incorporated in this food item:

EGCG: 5-500 mg/per serving
Protein hydrolysates: 1.5-15 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [%] |
|---|---|
| Five cereal flour | 56.8 |
| Water | 39.8 |
| Yeast | 2.3 |
| Salt | 1.1 |

The yeast is dissolved in a part of the water. All ingredients are mixed together to form a dough. Salt is added at the end of the kneading time. After fermentation, the dough is reworked and divided before a loaf is formed. Before baking, the surface of the loaf is brushed with water and sprinkled with flour.

Procedure:
Kneading:

| Spiral kneading system | 4 min 1$^{st}$ gear, 5 min 2$^{nd}$ gear |
|---|---|
| Dough proofing: | 60 min |
| Dough temperature: | 22-24° C. |
| Proofing time: | 30 min |

Baking:

| Oven: | Dutch type oven |
|---|---|
| Baking temperature: | 250/220° C. |
| Baking time: | 50-60 min |

EXAMPLE 7

Cookies Type Milano
Typical serving: 30 g
Active ingredients:

EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:

EGCG: 5-500 mg/per serving
Protein hydrolysates: 0.9-9 g/per serving
Ligustilide or other phthalides or herbal extracts containing ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [g] |
|---|---|
| Wheat Flour, type 550 | 41.0 |
| Sugar | 20.5 |
| Fat/Butter | 20.5 |
| Whole egg (liquid) | 18.0 |
| Lemon Flavor | q.s. |
| Baking agent | q.s. |

All ingredients are added slowly under mixing to form a sweet short pastry.

Afterwards, the pastry is kept cool (4° C.) for at least 2 hours before flattening the pastry to a thickness of approx. 5 mm. Pieces are cut out and brushed with egg yolk on the surface before baking.

Baking:

| Oven: | fan oven |
|---|---|
| Baking temperature: | 180° C. |
| Baking time: | 15 min |

EXAMPLE 8

Toast
Typical serving: 100 g
Active ingredients:

EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:

EGCG: 5-500 mg/per serving
Protein hydrolysates: 1.8-18 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [%] |
|---|---|
| Wheat Flour, type 550 | 55.4 |
| Water | 33.2 |
| Yeast | 2.8 |
| Salt | 1.1 |
| Fat/Butter | 5.5 |
| Malt | 0.6 |
| Emulsifier baking agent | 1.4 |

The yeast is dissolved in a part of the water. All ingredients are mixed together to form a dough. Salt is added at the end of the kneading time. Afterwards, the dough is reworked, divided and placed in a baking tin for fermentation. After baking, the loaf is unmoulded directly.

Procedure:
Kneading:

| Spiral kneading system | 5-6 min 1$^{st}$ gear; 3-4 min 2$^{nd}$ gear |
|---|---|
| Dough proofing: | none |
| Dough temperature: | 22-24° C. |
| Proofing time: | 40 min |

Baking:

| Oven: | Dutch type oven |
|---|---|
| Baking temperature: | 220° C. |
| Baking time: | 35-40 min |

EXAMPLE 9

Yoghurt—Set Type; 3.5% Fat
Typical serving: 225 g
Active ingredients:
EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:
EGCG: 5-500 mg/per serving
Protein hydrolysates: 1.5-15 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [%] |
|---|---|
| Full fat milk (3.8% fat) | 90.5 |
| Skimmed milk powder | 2.0 |
| Sugar | 5.0 |
| Culture | 2.5 |

The milk is heated to 35° C. before addition of milk powder, stabilizer, sugar and active ingredients. This mixture is heated to 65° C. to dissolve all ingredients. Then the mixture is homogenized in a high-pressure homogenizer ($p_1$=150 bar, $p_2$=50 bar) at 65° C. This emulsion is then pasteurized at 80° C. for 20 minutes. After cooling to 45° C. natural yoghurt/culture is added and mixed. Then this mixture is filled into cups and fermented at 45° C. for 3-4 hours until a pH of 4.3 is reached and then stored at 4° C.

EXAMPLE 10

Yoghurt—Stirred Type; 3.5% Fat
Typical serving: 225 g
EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:
EGCG: 5-500 mg/per serving
Protein hydrolysates: 0.3-3 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [%] |
|---|---|
| Full fat milk (3.8% fat) | 90.2 |
| Skimmed milk powder | 2.0 |
| Stabilizer | 0.3 |
| Sugar | 5.0 |
| Culture | 2.5 |

The milk is heated to 35° C. before addition of milk powder, stabilizer, sugar and active ingredients. This mixture is heated to 65° C. to dissolve all ingredients before homogenization in a high-pressure homogenizer ($p_1$=150 bar, $p_2$=50 bar) at 65° C. This emulsion is then pasteurized at 80° C. for 20 minutes. After cooling to 45° C. natural yoghurt/culture is added and mixed, followed by fermentation at 45° C. for 3-4 hours until a pH of 4.3 is reached. After cooling and stirring vigorously, the yoghurt is filled in cups and stored at 4° C.

EXAMPLE 11

Ice Cream; 8% Fat
Typical serving: 85 g
Active ingredients:
EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:
EGCG: 5-500 mg/per serving
Protein hydrolysates: 0.3-3 g/per serving
Ligustilide or other phthalides: 1-500 mg/per serving
Coenzyme Q-10: 1-400 mg/per serving
Resveratrol: 1-1000 mg/day
Pantethine: 20-800 mg/per serving
Phytanic acid: 20-2000 mg/per serving
Lipoic acid: 5-500 mg/per serving
Policosanol: 0.1-20 mg/per serving

| Other components: | [g] |
|---|---|
| Milk (3.7% fat) | 600.00 |
| Cream (35% fat) | 166.00 |
| Skim milk powder | 49.10 |
| Sugar | 109.00 |
| Glucose syrup 80% | 70.00 |
| Ice cream stabilizer | 5.00 |
| Flavor | q.s. |
| Color | q.s |

Sugar, skim milk powder and stabilizer are added to the milk and cream, mixed and heated to 45° C. Then the color as stock solution and the glucose syrup is added as well as the active ingredients. The mix is heated up and pasteurized (20 min, 80° C.). Then a homogenization step takes place. Afterwards the mix is cooled down under constant stirring and the flavor is added at 5° C. The mix maturated at 5° C. during at least 4 h and then passed through an ice cream machine (overrun ca. 100%). The ice cream is filled into cups and stored at −20 to −30° C.

EXAMPLE 12

Wine Gums
Active ingredients:
EGCG and protein hydrolysates and optionally one or more components selected from ligustilide or other phthalides or herbal extracts containing ligustilide or other phthalides, Coenzyme Q-10, resveratrol, pantethine, phytanic acid and lipoic acid are incorporated in this food item:
EGCG: 5-500 mg/per 30 g
Protein hydrolysates: 0.15-1.5 g/per serving
Ligustilide or other phthalides: 1-500 mg/per serving
Coenzyme Q-10: 1-400 mg/per 30 g
Resveratrol: 1-1000 mg/day
Pantethine: 20-800 mg/per 30 g
Phytanic acid: 20-2000 mg/per 30 g
Lipoic acid: 5-500 mg/per 30 g
Policosanol: 0.1-20 mg/per serving

| Other components: | [g] |
|---|---|
| Gelatin 200 Bloom | 80.0 |
| Water I | 125.0 |
| Sugar crys. | 290.0 |
| Water II | 120.0 |
| Glucose-syrup DE38 | 390.0 |
| Citric acid | 10.0 |
| Flavor | 2.0 |
| Color | q.s. |
| Yield ca | 1000.0 |

Disperse gelatin in water 1, stir and dissolve by heating over a stream bath or using a microwave. Mix sugar with water 11 and bring to boiling until a clear solution is obtained. Remove from heat source. Mix with glucose syrup while dissolved sugar solution is still hot. Slowly add the gelatin solution. Let rest until foam on surface can be removed and 60-65° C. is reached. Add flavor, citric acid and the color solution as well as active ingredients under stirring. Deposit into moulds printed into starch trays and let sit for at least 48 hours at RT. Remove starch powder and polish with oil or wax. Dry at RT and package into airtight pouches.

The invention claimed is:
1. A composition comprising
a blood glucose level maintaining amount of a combination of:
5 to 500 mg EGCG and a protein hydrolysate, wherein the protein hydrolysate is selected from the group consisting of:
a) a whey hydrolysate which comprises peptides wherein the molar fraction of peptides carrying a carboxy terminal proline is at least 8%;
b) a casein hydrolysate which comprises peptides wherein the molar fraction of peptide carrying a carboxy terminal proline is at least 25%;
c) a soy hydrolysate which comprises peptides wherein the molar fraction of peptide carrying a carboxy terminal proline is at least 20%;
d) a gluten hydrolysate which comprises peptides wherein the molar fraction of peptide carrying a carboxy terminal proline is at least 20%; and
e) a barley hydrolysate which comprises peptides wherein the molar fraction of peptide carrying a carboxy terminal proline is at least 20%,
and at least one of: ligustilide or other phthalides or herbal extracts containing ligustilide or other phthalides, coenzyme Q-q0, resveratrol, panthethine or a metabolite thereof, phytanic acid, lipoic acid, and policosanol.

2. A composition as in claim 1 wherein the protein hydrolysate comprises peptides, wherein the molar fraction of peptides (%) carrying a carboxy terminal proline is more than two times the molar fraction (%) of proline in the protein substrate used to generate the hydrolysate.

3. A composition as in claim 1 wherein the protein hydrolysate has a high content of tripeptides which are rich in proline at one end of the peptide.

4. A composition as in claim 1 for the treatment of type 2 diabetes mellitus (T2DM) in those individuals with pre-diabetes, or impaired glucose tolerance (IGT), or obesity, or established type 2 diabetes mellitus.

5. A composition as in claim 4 containing EGCG in an amount sufficient to administer to a subject a daily dosage of 0.3 mg per kg body weight to about 30 mg per kg body weight.

6. A composition as in claim 4 containing a protein hydrolysate in an amount sufficient to administer to a subject a daily dosage of 0.01 g per kg body weight to about 3 g per kg body weight.

7. A composition as in claim 4 comprising:
a) ligustilide or other phthalides or herbal extracts containing ligustilide or other phthalides; or
b) Coenzyme Q-10; or
c) resveratrol; or
d) ligustilide or other phthalides or herbal extracts containing ligustilide or other phthalides, and Coenzyme Q-10; or
e) ligustilide or other phthalides or herbal extracts containing ligustilide or other phthalides and resveratrol.

8. A composition as in claim 4 which is in dosage unit form.

9. A composition as in claim 8 wherein the dosage unit form is a solid dosage unit form.

10. A composition as in claim 4, wherein the composition is in the form of food or beverage or a supplement composition for inclusion within a food or beverage.

11. A food or beverage comprising
a blood glucose level maintaining amount of a combination of:
50 to 500 mg EGCG and a protein hydrolysate, selected from the group consisting of:
a) a whey hydrolysate which comprises peptides wherein the molar fraction of peptides carrying a carboxy terminal proline is at least 8%;
b) a casein hydrolysate which comprises peptides wherein the molar fraction of peptide carrying a carboxy terminal proline is at least 25%;
c) a soy hydrolysate which comprises peptides wherein the molar fraction of peptide carrying a carboxy terminal proline is at least 20%;
d) a gluten hydrolysate which comprises peptides wherein the molar fraction of peptide carrying a carboxy terminal proline is at least 20%; and
e) a barley hydrolysate which comprises peptides wherein the molar fraction of peptide carrying a carboxy terminal proline is at least 20%;
and at least one of: ligustilide or other phthalides or herbal extracts containing ligustilide or other phthalides, coenzyme Q-10, resveratrol, pantethine or a metabolite thereof, phytanic acid, lipoic acid, and policosanol.

12. A food or beverage as in claim 11 wherein the protein hydrolysate comprises peptides, wherein the molar fraction of peptides (%) carrying a carboxy terminal proline is more than two times the molar fraction (%) of proline in the protein substrate used to generate the hydrolysate.

13. A food or beverage as in claim 11 wherein the protein hydrolysate is a whey hydrolysate which comprises peptides wherein the molar fraction of peptides carrying a carboxy terminal proline is at least 8%, preferably at least 15%, more preferably from 30 to 70%.

14. A food or beverage as in claim 11 wherein the protein hydrolysate has a high content of tripeptides which are rich in proline at one end of the peptide.

15. A nutraceutical composition comprising
a blood glucose level maintaining amount of a combination of:
10 mg to 500 mg EGCG, a protein hydrolysate selected from the group consisting of:
a) a whey hydrolysate which comprises peptides wherein the molar fraction of peptides carrying a carboxy terminal proline is at least 8%;
b) a casein hydrolysate which comprises peptides wherein the molar fraction of peptide carrying a carboxy terminal proline is at least 25%;
c) a soy hydrolysate which comprises peptides wherein the molar fraction of peptide carrying a carboxy terminal proline is at least 20%;
d) a gluten hydrolysate which comprises peptides wherein the molar fraction of peptide carrying a carboxy terminal proline is at least 20%; and
e) a barley hydrolysate which comprises peptides wherein the molar fraction of peptide carrying a carboxy terminal proline is at least 20%;
and at least one of: ligustilide or other phthalides or herbal extracts containing ligustilide or other phthalides, coenzyme Q-10, resveratrol, pantethine or a metabolite thereof, phytanic acid, lipoic acid, and policosanol.

16. The nutraceutical composition as in claim 15, wherein said EGCG is in an amount sufficient to provide a daily dosage of 0.3 mg per kg body weight to about 30 mg per kg body weight of the subject to which it is to be administered,
the protein hydrolysate is in an amount sufficient to provide a daily dosage of 0.01 g per kg body weight to about 3 g per kg body weight of the subject to which it is to be administered,
the ligustilide or other phthalides or herbal extracts containing ligustilide or other phthalides or herbal extracts containing ligustilide or other phthalides are in an amount sufficient to provide a daily dosage of 0.01 mg of ligustilide or other phthalide per kg body weight to about 10 mg per kg body weight of the subject to which it is to be administered,
coenzyme Q-10 is in an amount sufficient to provide a daily dosage of 0.01 mg per kg body weight to about 50 mg per kg body weight of the subject to which it is to be administered, and
resveratrol is in an amount sufficient to provide a daily dosage of 0.01 mg per kg body weight to about 30 mg per kg body weight of the subject to which it is to be administered.

17. The nutraceutical composition as in claim 15 in the form of a food or beverage, or a supplement composition for food or beverage.

18. The nutraceutical composition as in claim 15 which is intended for the treatment of both type 1 and 2 diabetes, impaired glucose tolerance (IGT) or obesity.

19. The nutraceutical composition as in claim 15 which is a pharmaceutical composition for the treatment of both type 1 and 2 diabetes, and for the prevention of type 2 diabetes in those individuals with pre-diabetes, or impaired glucose tolerance (IGT) or obesity.

20. A method for the treatment of both type 1 and 2 diabetes, or impaired glucose tolerance (IGT) or obesity which comprises administering to a subject in need of such treatment an effective amount of the composition according to claim 1.

* * * * *